US012758773B2

(12) United States Patent
Van Den Heuvel et al.

(10) Patent No.: US 12,758,773 B2
(45) Date of Patent: Oct. 13, 2026

(54) INTRAOPERATIVE GUIDANCE FOR IMPLANTABLE TRANSDUCERS

(71) Applicant: Cochlear Limited, Macquarie University (AU)

(72) Inventors: Koen Erik Van Den Heuvel, Hove (BE); Antonin Rambault, Mechelen (BE)

(73) Assignee: Cochlear Limited, Macquarie University (AU)

( * ) Notice: Subject to any disclaimer, the term of this patent is extended or adjusted under 35 U.S.C. 154(b) by 334 days.

(21) Appl. No.: 18/707,023

(22) PCT Filed: Oct. 31, 2022

(86) PCT No.: PCT/IB2022/060475
§ 371 (c)(1),
(2) Date: May 2, 2024

(87) PCT Pub. No.: WO2023/084358
PCT Pub. Date: May 19, 2023

(65) Prior Publication Data

US 2026/0158272 A1 Jun. 11, 2026

Related U.S. Application Data

(60) Provisional application No. 63/277,333, filed on Nov. 9, 2021.

(51) Int. Cl.
*A61N 1/36* (2006.01)
*A61B 5/00* (2006.01)

(52) U.S. Cl.
CPC ........ *A61N 1/36039* (2017.08); *A61B 5/6817* (2013.01); *A61B 5/6832* (2013.01); *A61B 2562/0204* (2013.01)

(58) Field of Classification Search
CPC .............................. A61N 1/36039; A61N 1/36
See application file for complete search history.

(56) References Cited

U.S. PATENT DOCUMENTS 6,342,035 B1 1/2002 Kroll et al.
6,712,754 B2 3/2004 Miller et al.
(Continued)

FOREIGN PATENT DOCUMENTS

EP 0 923 392 B1 11/2005
KR 10-2013-0133790 A 12/2013
(Continued)

OTHER PUBLICATIONS

International Search Report and Written Opinion in counterpart International Application No. PCT/IB2022/060475, mailed Feb. 13, 2023, 8 pages.
(Continued)

*Primary Examiner* — Unsu Jung
*Assistant Examiner* — Fiona M Kowalkowski
(74) *Attorney, Agent, or Firm* — Edell, Shapiro & Finnan, LLC

(57) ABSTRACT

Presented herein are techniques for monitoring the bonding of an implantable transducer, such as an implantable sound sensor or implantable actuator, to tissue of a recipient. More specifically, the sensitivity of the implantable transducer is monitored during the bonding process using signals captured/received by the implantable transducer. The signals captured by the implantable transducer are analyzed to determine whether and/or when the implantable sound sensor is bonded to the tissue.

22 Claims, 16 Drawing Sheets

(56) References Cited

U.S. PATENT DOCUMENTS

| | | | |
|---|---|---|---|
| 6,879,693 B2 | 4/2005 | Miller et al. | |
| 6,997,864 B2 | 2/2006 | Conn et al. | |
| 7,137,946 B2 | 11/2006 | Waldmann | |
| 7,582,052 B2 | 9/2009 | Waldmann | |
| 8,144,884 B2 | 3/2012 | Van den Heuvel et al. | |
| 9,167,355 B2 | 10/2015 | Buehlmann et al. | |
| 9,525,949 B1 | 12/2016 | Glumac | |
| 9,986,947 B2 | 6/2018 | Thibaut et al. | |
| 10,743,812 B1 | 8/2020 | Glumac et al. | |
| 2002/0026091 A1 | 2/2002 | Leysieffer | |
| 2002/0048374 A1 | 4/2002 | Soli et al. | |
| 2003/0161481 A1 | 8/2003 | Miller et al. | |
| 2013/0116497 A1 | 5/2013 | Vermeiren et al. | |
| 2014/0163692 A1* | 6/2014 | Van Den Heuvel | H04R 25/606 623/23.62 |
| 2018/0235812 A1* | 8/2018 | Van Den Heuvel | H04R 25/606 |
| 2018/0376255 A1* | 12/2018 | Parker | H04R 25/00 |
| 2020/0296520 A1 | 9/2020 | Meskens et al. | |
| 2021/0051418 A1 | 2/2021 | Waldmann et al. | |
| 2021/0099810 A1 | 4/2021 | Leroux | |

FOREIGN PATENT DOCUMENTS

| | | |
|---|---|---|
| WO | 2009152528 A1 | 12/2009 |
| WO | 2009155650 A1 | 12/2009 |
| WO | 2013068919 A2 | 5/2013 |
| WO | 2016030759 A1 | 3/2016 |
| WO | 2018154397 A1 | 8/2018 |
| WO | 2020084395 A1 | 4/2020 |

OTHER PUBLICATIONS

Extended European Search Report in counterpart European Application No. 22892221.7-1207, mailed Sep. 16, 2025, 11 pages.

Frank C. Beall: "Subsurface sensing of properties and defects in wood and wood products", Subsurface Sensing Technologies and Applications, vol. 1, No. 2, Jan. 1, 2000 (Jan. 1, 2000), pp. 181-204, XP055012433, ISSN: 1566-0184, DOI: 10.1023/A:1010135009428.

Claus R O et al: "Embedded Optical Fiber Sensors for Materials Evalution", Journal of Nondestructive Evaluation, Plenum Publishing Corporationt. New York, US, vol. 8, No. 2, Jun. 1, 1989 (Jun. 1, 1989), pp. 135-145, XP000162097, ISSN: 0195-9298, DOI: 10.1007/BF00565637.

* cited by examiner

INTRAOPERATIVE GUIDANCE FOR IMPLANTABLE TRANSDUCERS

BACKGROUND

Field of the Invention

The present invention relates generally to implantable transducers.

Related Art

Medical devices have provided a wide range of therapeutic benefits to recipients over recent decades. Medical devices can include internal or implantable components/devices, external or wearable components/devices, or combinations thereof (e.g., a device having an external component communicating with an implantable component). Medical devices, such as traditional hearing aids, partially or fully-implantable hearing prostheses (e.g., bone conduction devices, mechanical stimulators, cochlear implants, etc.), pacemakers, defibrillators, functional electrical stimulation devices, and other medical devices, have been successful in performing lifesaving and/or lifestyle enhancement functions and/or recipient monitoring for a number of years.

The types of medical devices and the ranges of functions performed thereby have increased over the years. For example, many medical devices, sometimes referred to as "implantable medical devices," now often include one or more instruments, apparatus, sensors, processors, controllers or other functional mechanical or electrical components that are permanently or temporarily implanted in a recipient. These functional devices are typically used to diagnose, prevent, monitor, treat, or manage a disease/injury or symptom thereof, or to investigate, replace or modify the anatomy or a physiological process. Many of these functional devices utilize power and/or data received from external devices that are part of, or operate in conjunction with, implantable components.

SUMMARY

In one aspect, a method is provided. The method comprises: delivering sound signals to an ear of a recipient, wherein an implantable sound sensor arrangement is mechanically attached to an internal structure of the ear via a bonding agent; at least while the bonding agent is curing, capturing the sound signals with the implantable sound sensor arrangement; generating, at the implantable sound sensor arrangement, output signals representing the sound signals captured by the implantable sound sensor arrangement; and monitoring a sensitivity of the implantable sound sensor arrangement based on the output signals generated by the implantable sound sensor arrangement.

In another aspect, one or more non-transitory computer readable storage media are provided. The one or more non-transitory computer readable storage media comprise instructions that, when executed by a processor, cause the processor to: receive sound signals captured by an implantable transducer bonded to human tissue of a recipient; and determine a sensitivity of the implantable transducer based on sound signals captured by the implantable transducer.

In another aspect, a method is provided. The method comprises: capturing sound signals with an implantable sound sensor bonded to tissue of a recipient; converting the sound signals to output signals; and evaluating an effectivity of a bond between the implantable sound sensor and the tissue based on the output signals.

BRIEF DESCRIPTION OF THE DRAWINGS

Embodiments of the present invention are described herein in conjunction with the accompanying drawings, in which.

DETAILED DESCRIPTION

Presented herein are techniques for monitoring the bonding of an implantable transducer, such as an implantable sound sensor or implantable actuator, to tissue of a recipient. More specifically, the sensitivity of the implantable transducer is monitored during the bonding process using signals captured/received by the implantable transducer. The signals captured by the implantable transducer are analyzed to determine whether, when, and/or how the implantable sound sensor is bonded to the tissue.

As such, presented herein are techniques to monitor the curing process of a bonding agent uses with an implantable transducer. The system measures the performance of the implantable transducer and provides information or clinical recommendations based on the measurements. For example, clinical recommendations can be generated to initiate corrective actions that can improve the situation, such as dislocation of the incudostapedial joint. In general, the techniques presented herein provide feedback to a user (e.g., surgeon) about the performance of an implantable transducer during the bonding process, which reduces the risks of poor performance, reduces the need for a revision surgery, and result in more consistent surgical outcomes across a population of recipients.

Merely for ease of description, the techniques presented herein are primarily described with reference to a specific component of an implantable medical device, namely an implantable sound sensor (microphone), forming part of an implantable auditory prosthesis. It is to be appreciated that the techniques presented herein may also be partially or fully implemented by other types of implantable medical devices having implantable transducers configured to be fixed to a recipient. For example, the techniques presented herein may be implemented with other types of auditory prostheses, such as cochlear implants, middle ear auditory prostheses, bone conduction devices, electro-acoustic prostheses, auditory brain stimulators, direct acoustic stimulations, combinations or variations thereof, etc. The techniques presented herein may also be implemented by dedicated tinnitus therapy devices and tinnitus therapy device systems. In further embodiments, the presented herein may also be implemented by, or used in conjunction with, vestibular devices (e.g., vestibular implants), visual devices (i.e., bionic eyes), sensors, pacemakers, drug delivery systems, defibrillators, functional electrical stimulation devices, catheters, seizure devices (e.g., devices for monitoring and/or treating epileptic events), sleep apnea devices, electroporation devices, etc.

Figure 1A:
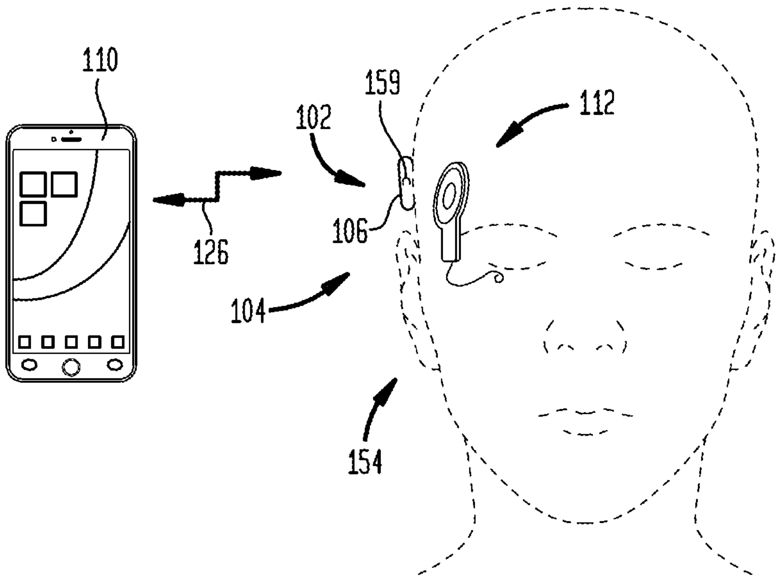
FIG. 1A is a schematic diagram illustrating a cochlear implant system with which aspects of the techniques presented herein can be implemented.
Figure 1B:
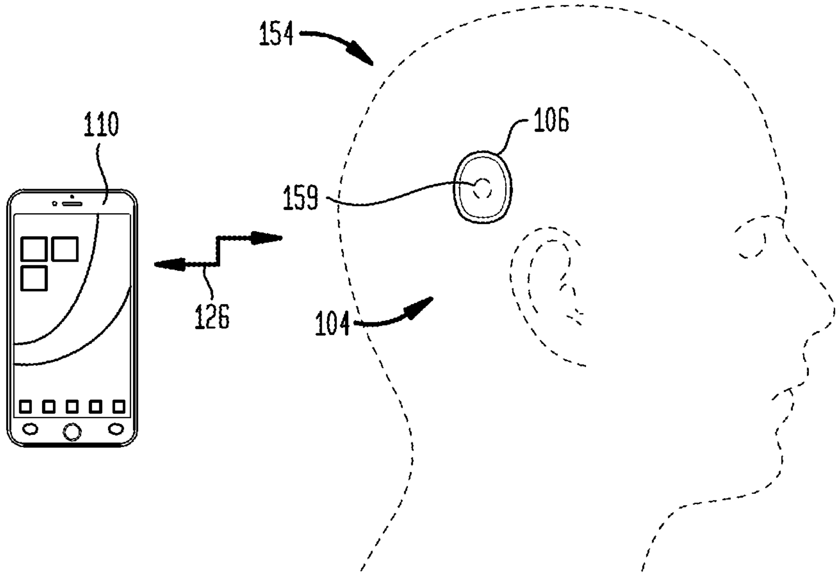
FIG. 1B is a side view of a recipient wearing a sound processing unit of the cochlear implant system of FIG. 1A.
Figure 1C:
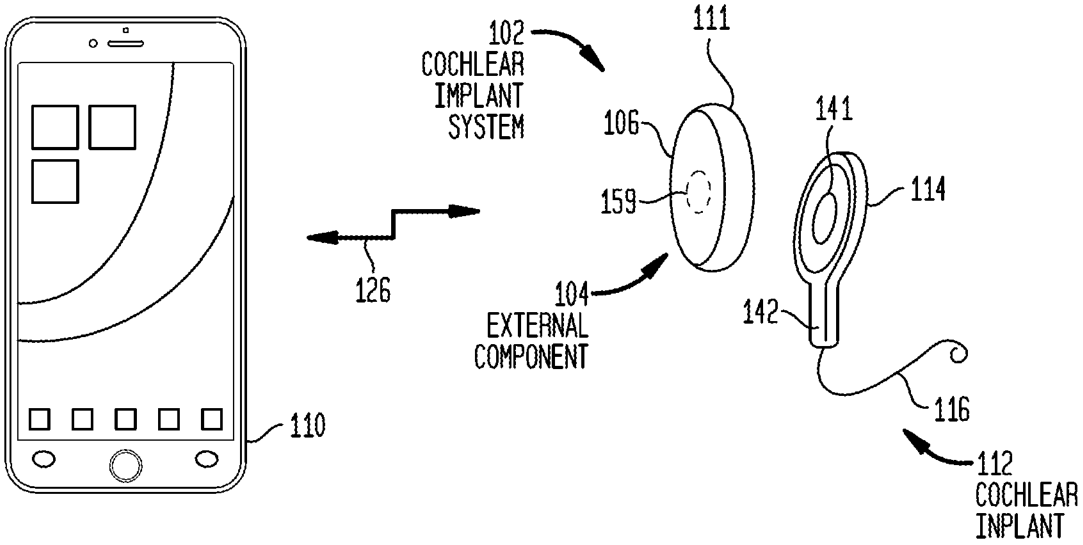
FIG. 1C is a schematic view of components of the cochlear implant system of FIG. 1A.
Figure 1D:
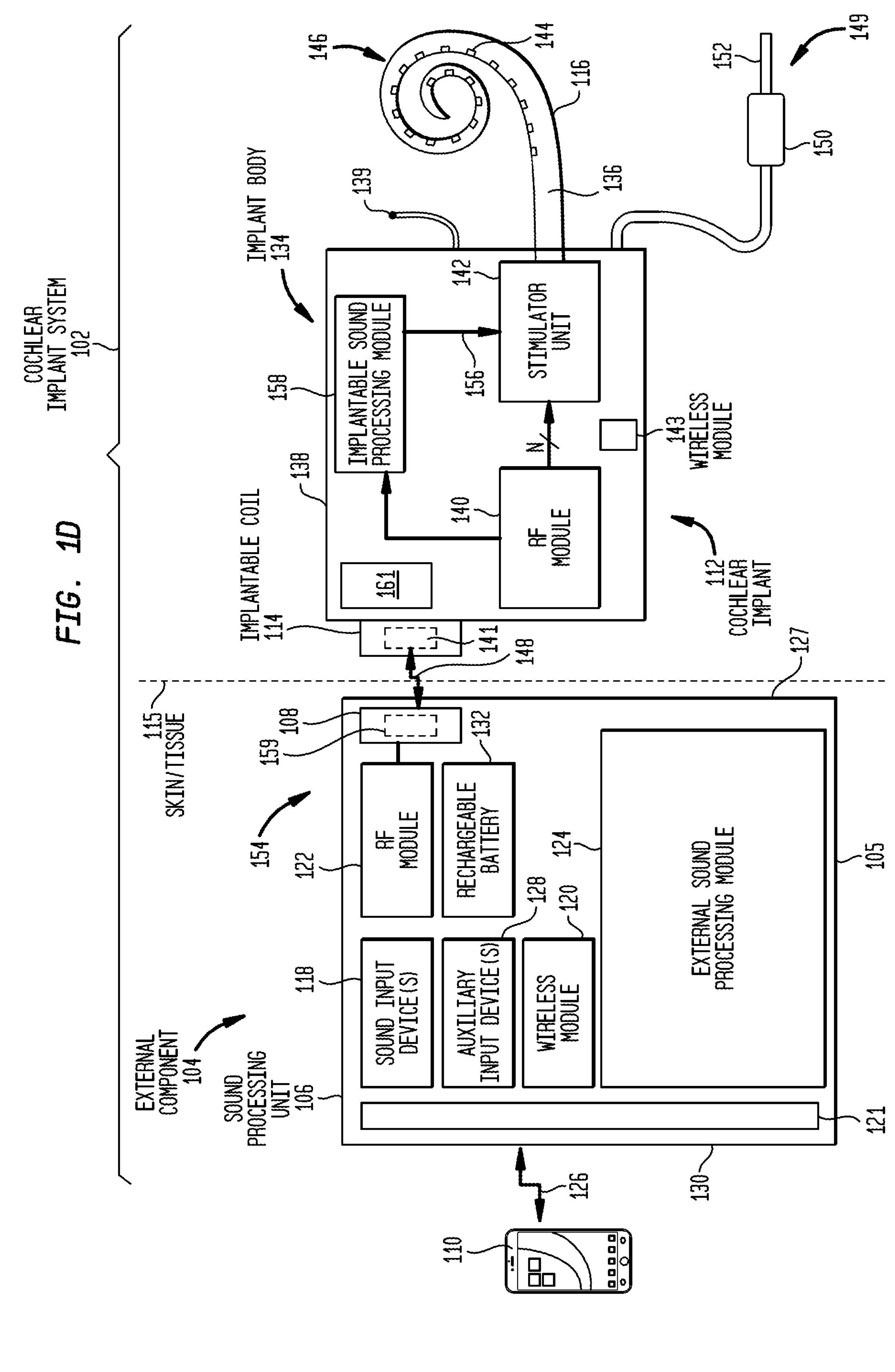
FIG. 1D is a block diagram of the cochlear implant system of FIG. 1A.

FIGS. 1A-1D illustrates an example cochlear implant system 102 with which aspects of the techniques presented herein can be implemented. The cochlear implant system 102 comprises an external component 104 and an implantable component 112. In the examples of FIGS. 1A-1D, the implantable component is sometimes referred to as a "cochlear implant." FIG. 1A illustrates the cochlear implant 112 implanted in the head 154 of a recipient, while FIG. 1B is a schematic drawing of the external component 104 worn on the head 154 of the recipient. FIG. 1C is another schematic view of the cochlear implant system 102, while FIG. 1D illustrates further details of the cochlear implant system 102. For ease of description, FIGS. 1A-1D will generally be described together.

Cochlear implant system 102 includes an external component 104 that is configured to be directly or indirectly attached to the body of the recipient and an implantable component 112 configured to be implanted in the recipient. In the examples of FIGS. 1A-1D, the external component 104 comprises a sound processing unit 106, while the cochlear implant 112 includes an implantable coil 114, an implant body 134, and an elongate stimulating assembly 116 configured to be implanted in the recipient's cochlea.

In the example of FIGS. 1A-1D, the sound processing unit 106 is an off-the-ear (OTE) sound processing unit, sometimes referred to herein as an OTE component, which is configured to send data and power to the implantable component 112. In general, an OTE sound processing unit is a component having a generally cylindrically shaped housing 111 and which is configured to be magnetically coupled to the recipient's head (e.g., includes an integrated external magnet 159 configured to be magnetically coupled to an implantable magnet 141 in the implantable component 112). The OTE sound processing unit 106 also includes an integrated external (headpiece) coil 108 that is configured to be inductively coupled to the implantable coil 114.

It is to be appreciated that the OTE sound processing unit 106 is merely illustrative of the external devices that could operate with implantable component 112. For example, in alternative examples, the external component may comprise a behind-the-ear (BTE) sound processing unit or a micro-BTE sound processing unit and a separate external. In general, a BTE sound processing unit comprises a housing that is shaped to be worn on the outer ear of the recipient and is connected to the separate external coil assembly via a cable, where the external coil assembly is configured to be magnetically and inductively coupled to the implantable coil 114. It is also to be appreciated that alternative external components could be located in the recipient's ear canal, worn on the body, etc.

As noted above, the cochlear implant system 102 includes the sound processing unit 106 and the cochlear implant 112. However, as described further below, the cochlear implant 112 can operate independently from the sound processing unit 106, for at least a period, to stimulate the recipient. For example, the cochlear implant 112 can operate in a first general mode, sometimes referred to as an "external hearing mode," in which the sound processing unit 106 captures sound signals which are then used as the basis for delivering stimulation signals to the recipient. The cochlear implant 112 can also operate in a second general mode, sometimes referred as an "invisible hearing" mode, in which the sound processing unit 106 is unable to provide sound signals to the cochlear implant 112 (e.g., the sound processing unit 106 is not present, the sound processing unit 106 is powered-off, the sound processing unit 106 is malfunctioning, etc.). As such, in the invisible hearing mode, the cochlear implant 112 captures sound signals itself via implantable sound sensors and then uses those sound signals as the basis for delivering stimulation signals to the recipient. Further details regarding operation of the cochlear implant 112 in the external hearing mode are provided below, followed by details regarding operation of the cochlear implant 112 in the invisible hearing mode. It is to be appreciated that reference to the external hearing mode and the invisible hearing mode is merely illustrative and that the cochlear implant 112 could also operate in alternative modes.

In FIGS. 1A and 1C, the cochlear implant system 102 is shown with an external device 110, configured to implement aspects of the techniques presented. The external device 110 is a computing device, such as a computer (e.g., laptop, desktop, tablet), a mobile phone, remote control unit, etc. As described further below, the external device 110 comprises a telephone enhancement module that, as described further below, is configured to implement aspects of the auditory rehabilitation techniques presented herein for independent telephone usage. The external device 110 and the cochlear implant system 102 (e.g., OTE sound processing unit 106 or the cochlear implant 112) wirelessly communicate via a bi-directional communication link 126. The bi-directional communication link 126 may comprise, for example, a short-range communication, such as Bluetooth link, Bluetooth Low Energy (BLE) link, a proprietary link, etc.

Returning to the example of FIGS. 1A-1D, the OTE sound processing unit 106 comprises one or more input devices that are configured to receive input signals (e.g., sound or data signals). The one or more input devices include one or more sound input devices 118 (e.g., one or more external microphones, audio input ports, telecoils, etc.), one or more auxiliary input devices 128 (e.g., audio ports, such as a Direct Audio Input (DAI), data ports, such as a Universal Serial Bus (USB) port, cable port, etc.), and a wireless transmitter, receiver, and/or transceiver, referred to as a wireless module 120 (e.g., for communication with the external device 110). However, it is to be appreciated that one or more input devices may include additional types of input devices and/or less input devices.

The OTE sound processing unit 106 also comprises the external coil 108, a charging coil 130, a closely-coupled transmitter, receiver, and/or transceiver, referred to as RF module 122, at least one rechargeable battery 132, and an external sound processing module 124. The external sound processing module 124 may comprise, for example, one or more processors and a memory device (memory) that includes sound processing logic. The memory device may comprise any one or more of: Non-Volatile Memory (NVM), Ferroelectric Random Access Memory (FRAM), read only memory (ROM), random access memory (RAM), magnetic disk storage media devices, optical storage media devices, flash memory devices, electrical, optical, or other physical/tangible memory storage devices. The one or more processors are, for example, microprocessors or microcontrollers that execute instructions for the sound processing logic stored in memory device.

The implantable component 112 comprises an implantable main module (implant body) 134, a lead region 136, and the intracochlear stimulating assembly 116, all configured to be implanted under the skin/tissue (tissue) 115 of the recipient. The implant body 134 generally comprises a hermetically-sealed housing 138 in which an RF module 140 (e.g., an RF receiver, and/or transceiver), a stimulator unit 142, a wireless module 143, an implantable sound processing unit 158, and a rechargeable battery 161 are disposed. The implant body 134 also includes the internal/implantable coil 114 that is generally external to the housing 138, but which is connected to the RF module 140 via a hermetic feedthrough (not shown in FIG. 1D).

As noted, stimulating assembly 116 is configured to be at least partially implanted in the recipient's cochlea. Stimulating assembly 116 includes a plurality of longitudinally spaced intracochlear electrical stimulating contacts (electrodes) 144 that collectively form a contact or electrode array 146 for delivery of electrical stimulation (current) to the recipient's cochlea.

Stimulating assembly 116 extends through an opening in the recipient's cochlea (e.g., cochleostomy, the round window, etc.) and has a proximal end connected to stimulator unit 142 via lead region 136 and a hermetic feedthrough (not shown in FIG. 1D). Lead region 136 includes a plurality of conductors (wires) that electrically couple the electrodes 144 to the stimulator unit 142. The implantable component 112 also includes an electrode outside of the cochlea, sometimes referred to as the extra-cochlear electrode (ECE) 139.

As noted, the cochlear implant system 102 includes the external coil 108 and the implantable coil 114. The external magnet 141 is fixed relative to the external coil 108 and the implantable magnet 141 is fixed relative to the implantable coil 114. The magnets fixed relative to the external coil 108 and the implantable coil 114 facilitate the operational alignment of the external coil 108 with the implantable coil 114. This operational alignment of the coils enables the external component 104 to transmit data and power to the implantable component 112 via a closely-coupled wireless link 148 formed between the external coil 108 with the implantable coil 114. In certain examples, the closely-coupled wireless link 148 is a radio frequency (RF) link. However, various other types of energy transfer, such as infrared (IR), electromagnetic, capacitive, and inductive transfer, may be used to transfer the power and/or data from an external component to an implantable component and, as such, FIG. 1D illustrates only one example arrangement.

As noted above, sound processing unit 106 includes the external sound processing module 124. The external sound processing module 124 is configured to convert received input signals (received at one or more of the input devices) into output signals for use in stimulating a first ear of a recipient (i.e., the external sound processing module 124 is configured to perform sound processing on input signals received at the sound processing unit 106). Stated differently, the one or more processors in the external sound processing module 124 are configured to execute sound processing logic in memory to convert the received input signals into output signals that represent electrical stimulation for delivery to the recipient.

As noted, FIG. 1D illustrates an embodiment in which the external sound processing module 124 in the sound processing unit 106 generates the output signals. In an alternative embodiment, the sound processing unit 106 can send less processed information (e.g., audio data) to the implantable component 112 and the sound processing operations (e.g., conversion of sounds to output signals) can be performed by a processor within the implantable component 112.

Returning to the specific example of FIG. 1D, the output signals are provided to the RF module 122, which transcutaneously transfers the output signals (e.g., in an encoded manner) to the implantable component 112 via external coil 108 and implantable coil 114. That is, the output signals are received at the RF module 140 via implantable coil 114 and provided to the stimulator unit 142. The stimulator unit 142 is configured to utilize the output signals to generate electrical stimulation signals (e.g., current signals) for delivery to the recipient's cochlea. In this way, cochlear implant system 102 electrically stimulates the recipient's auditory nerve cells, bypassing absent or defective hair cells that normally transduce acoustic vibrations into neural activity, in a manner that causes the recipient to perceive one or more components of the received sound signals.

As detailed above, in the external hearing mode the cochlear implant 112 receives processed sound signals from the sound processing unit 106. However, in the invisible hearing mode, the cochlear implant 112 is configured to capture and process sound signals for use in electrically stimulating the recipient's auditory nerve cells. In particular, the cochlear implant 112 includes at least an implantable sound sensor arrangement 149 that, in this example, comprising an implantable sound sensor 150 and a coupling member (coupling) 152. In alternative embodiment, the implantable sound sensor arrangement 149 could be an implantable sound sensor without a coupling member. In addition, as noted above, the cochlear implant 112 also comprises the implantable sound processing module 158 and the rechargeable battery 161.

Similar to the external sound processing module 124, the implantable sound processing module 158 may comprise, for example, one or more processors and a memory device (memory) that includes sound processing logic. The memory device may comprise any one or more of: Non- Volatile Memory (NVM), Ferroelectric Random Access Memory (FRAM), read only memory (ROM), random access memory (RAM), magnetic disk storage media devices, optical storage media devices, flash memory devices, electrical, optical, or other physical/tangible memory storage devices. The one or more processors are, for example, microprocessors or microcontrollers that execute instructions for the sound processing logic stored in memory device.

In the invisible hearing mode, the implantable sound sensor 150, potentially in cooperation with one or more other implantable sensors, such as an implantable vibration sensor (not shown in FIGS. 1A-1D), is configured to detect/capture signals (e.g., acoustic sound signals, vibrations, etc.), which are provided to the implantable sound processing module 158. The implantable sound processing module 158 is configured to convert received input signals (received at the implantable sound sensor 150) into electrical signals, sometimes referred to herein as sensed, received, or captured sound signals, for use in stimulating the first ear of a recipient (i.e., the processing module 158 is configured to perform sound processing operations). Stated differently, the one or more processors in implantable sound processing module 158 are configured to execute sound processing logic in memory to convert the received sound signals into output signals 156 that are provided to the stimulator unit 142. The stimulator unit 142 is configured to utilize the output signals 156 to generate electrical stimulation signals (e.g., current signals) for delivery to the recipient's cochlea, thereby bypassing the absent or defective hair cells that normally transduce acoustic vibrations into neural activity.

It is to be appreciated that the above description of the so-called external hearing mode and the so-called invisible hearing mode are merely illustrative and that the cochlear implant system 102 could operate differently in different embodiments. For example, in one alternative implementation of the external hearing mode, the cochlear implant 112 could use signals captured by the sound input devices 118 and the implantable sound sensor 150 in generating stimulation signals for delivery to the recipient. In other embodiments, the cochlear implant 112 could operate substantially or completely without the external component 104. That is, in such embodiments, the cochlear implant 112 could operate substantially or completely in the invisible hearing mode using the rechargeable battery 161. The rechargeable battery 161 would be recharged via an external charging device.

Figure 2A:
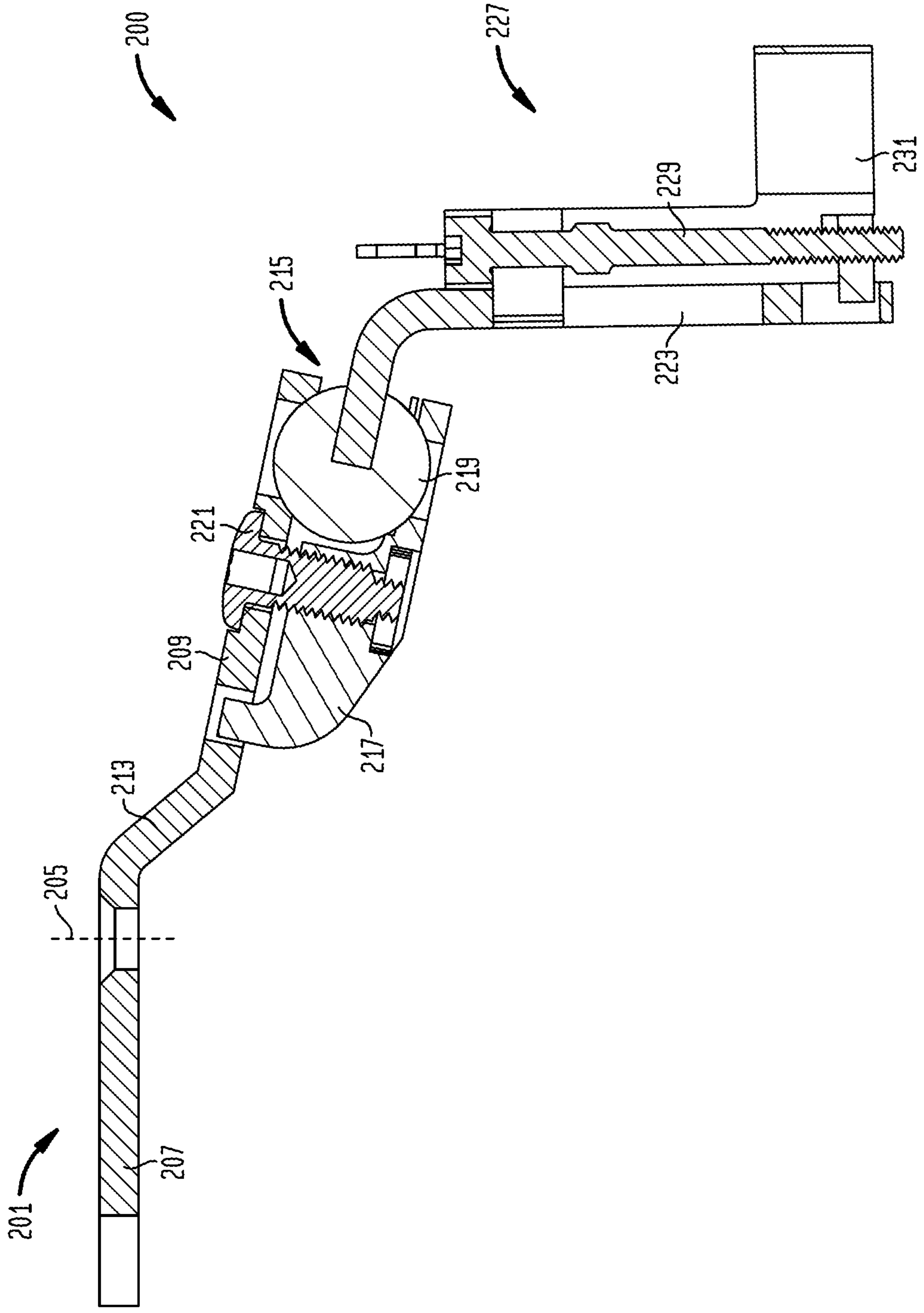
FIGS. 2A and 2B are side sectional and top perspective views, respectively, of a bracket for use with an implantable sound sensor.
Figure 2B:
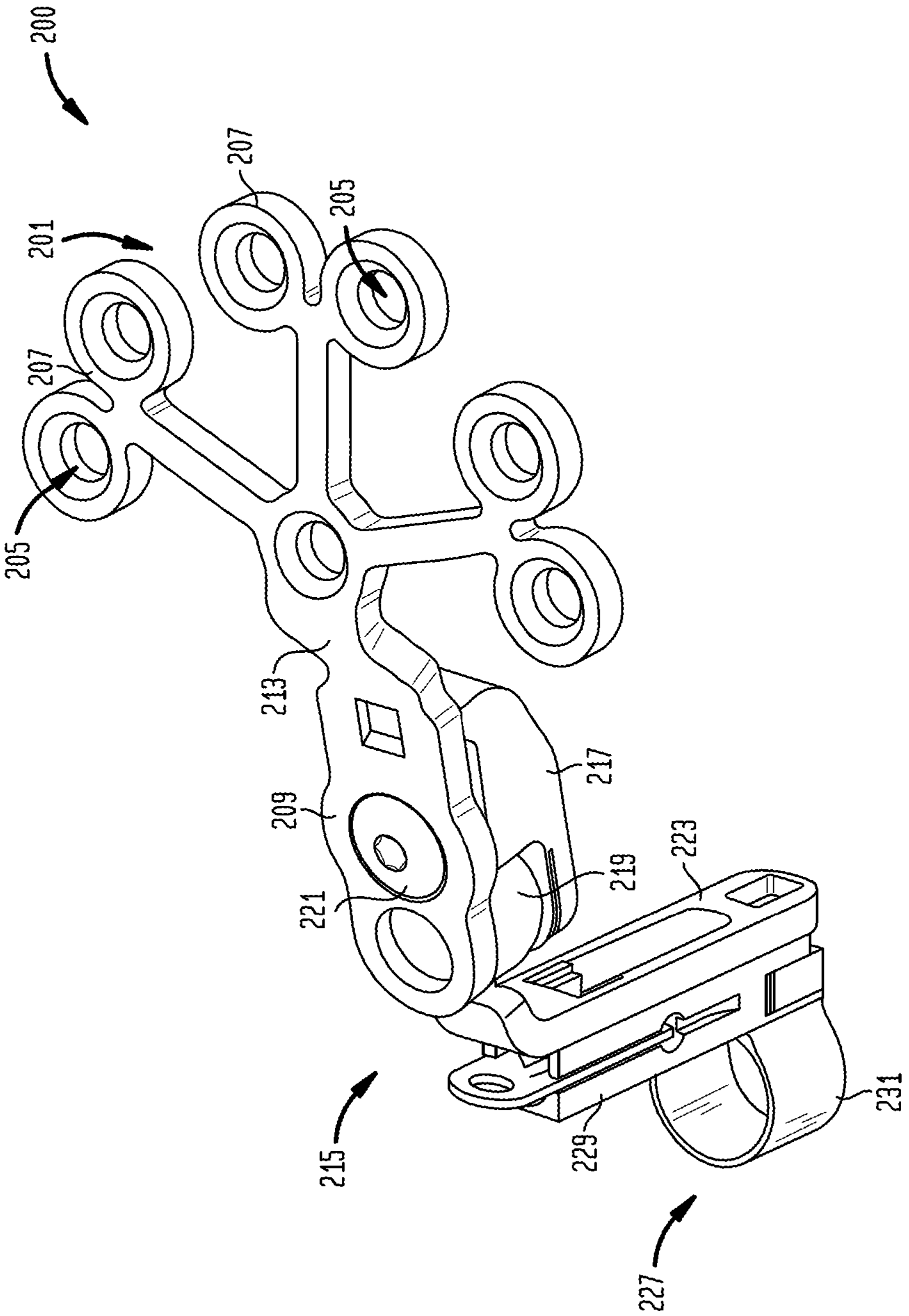

As noted, the implantable sound sensor 150 is implanted in a recipient and, in certain embodiments, is mechanically attached/coupled to tissue (e.g., bones) of the recipient via a coupling member (coupling) 152. For example, the implantable sound sensor 150 can be mechanically coupled to an internal ear structure of the recipient's ear, such as to the recipient's middle ear bones (ossicles), the recipient's inner ear (e.g., cochlea), etc. The mechanical coupling of the implantable sound sensor 150 to selected tissue of the recipient enables the implantable sound sensor 150 to capture sound signals, despite the fact that the implantable sound sensor 150 is disposed within the body of the recipient. FIGS. 2A-2B illustrate an example system for implantation of the implantable sound sensor 150 within a recipient.

More specifically, FIGS. 2A and 2B are side sectional and top perspective views, respectively, of a bracket 200 for use with an implantable transducer, in accordance with certain embodiments presented herein. FIGS. 2A and 2B are described simultaneously. The bracket 200 includes a number of subparts or components that aid in securing a transducer to a recipient such that, for example, the transducer can capture sound signals from the recipient's internal ear structure, the transducer can deliver stimulation signals to the recipient's internal ear structure, etc. A fixation element 201 defines a number of openings 205 therein for receipt of bone screws. The fixation element 201 includes a bone plate 207 that defines the openings 205. The bone plate 207 is connected to a clamp plate 209 via a transition 213. Each portion of the fixation element 201, the bone plate 207, clamp plate 209, and transition 213 can be configured as required or desired for a particular application. In general, the fixation element 201 is sized and configured so as to be secured to the skull of the recipient. An adjustable joint 215 is used to further align an acoustic actuator (not shown) with the desired internal ear anatomy, as described in further detail below. The adjustable joint 215 includes a ball clamp 217 that, along with the clamp plate 209, defines a socket and secures a ball 219. A position of the ball 219 can be set utilizing a clamp screw 221. A ball plate 223 extends from the ball 219 and enables positioning of an actuator assembly 227 that includes an actuator plate 229 and an actuator clamp 231 for retaining the acoustic actuator.

Figure 3:
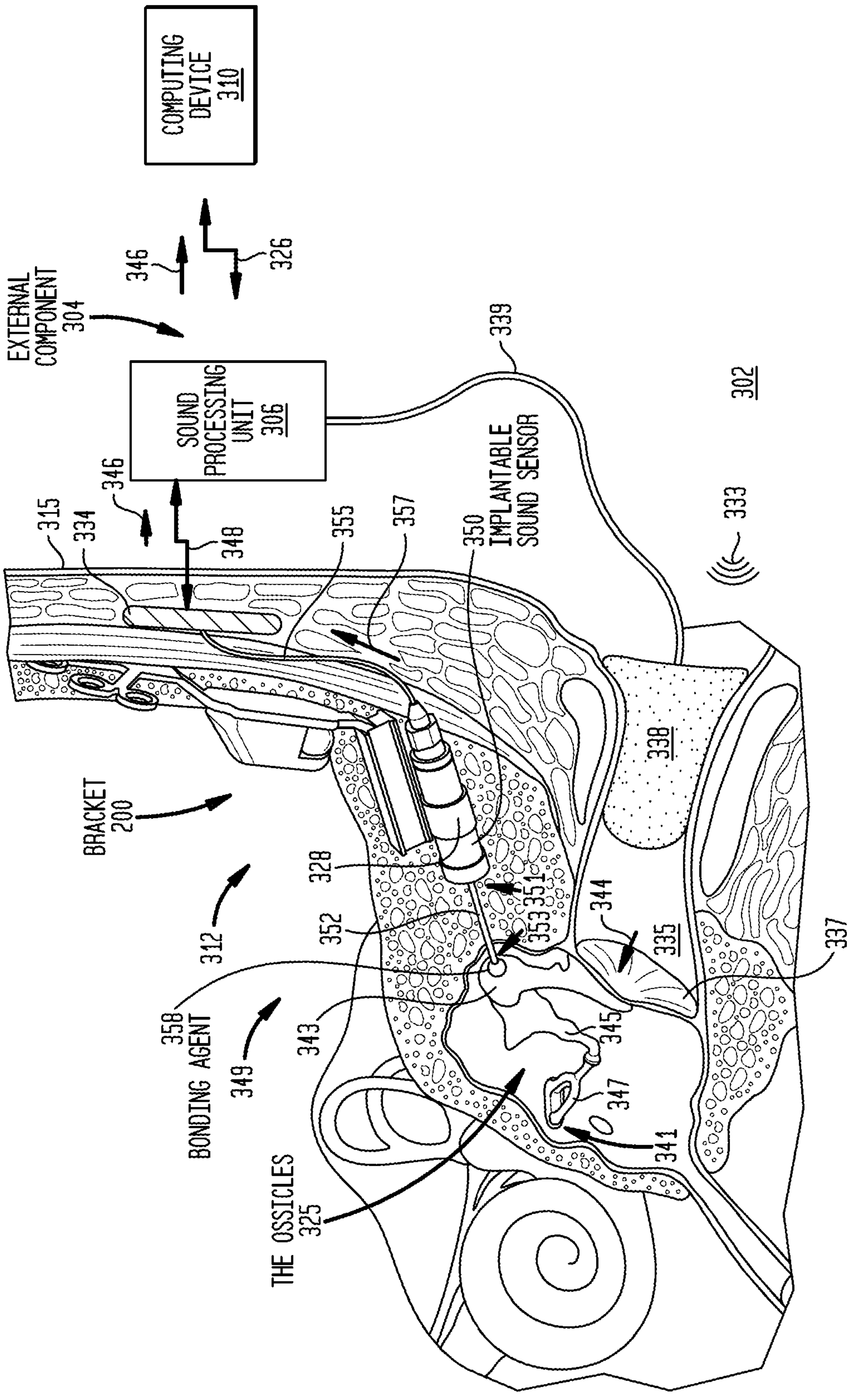
FIG. 3 is a schematic diagram illustrating aspects of the techniques presented herein.

FIG. 3 is schematic diagram illustrating an implantable transducer in the form of an implantable sound sensor (microphone) 350 implanted in a recipient R. In this example, implantable sound sensor 350 is mounted with the bracket 200, as described above, via the actuator ring 231. Certain subparts or components of the bracket 200 are described above with regard to FIGS. 2A and 2B and thus are not described further.

As shown, the implantable sound sensor 350 is attached to the recipient's middle ear bones, namely the ossicles 325, which include the malleus 343, the incus 345, and the stapes 347, via an attachment member or coupling member 352. That is, the coupling member 352 has a proximal end 351 attached the implantable sound sensor 350, and a distal end 353 rigidly bonded (e.g., secured/fixed) to the ossicles 325 via, for example, a biocompatible cement, biocompatible rigid adhesive, etc., collectively and generally referred to herein as "bonding agent 358." The coupling member 352 can be integrated with the implantable sound sensor 350 (e.g., part of the sound sensor) or can be separate from the sound sensor and mechanically attached there to.

The implantable sound sensor 350 and the coupling member 352 are sometimes collectively referred to herein as an "implantable sound sensor arrangement" 349. However, as used herein an implantable sound sensor arrangement could include only an implantable sound sensor directly attached to tissue of a recipient. More generally, the term "implantable sound sensor arrangement" is used herein to reference to any implantable transducer (e.g., sound sensor, vibration sensor, actuator, etc.) that is directly attached to tissue of a recipient or that is attached to a recipient via one or more intermediate devices, such as a coupling member.

In the example of FIG. 3, the implantable sound sensor 350 is electrically connected to an implantable main module 334 via a lead 355. In certain embodiments, the implantable main module 334 can comprise sound processing components (not shown in FIG. 3), while in other embodiments the sound processing components can be external to the body of the recipient.

As shown, an acoustic pressure or sound wave (sound signal) 333 is collected by auricle (not shown in FIG. 3) and channeled into and through ear canal 335. Disposed across the distal end of ear canal 335 is the tympanic membrane 337 which vibrates in response to the sound wave 333. This vibration is coupled to oval window or fenestra ovalis 341 via the ossicles 325, which serve to filter and amplify the sound wave. As noted above, and as shown in FIG. 3, the implantable sound sensor 350 is mechanically coupled to the ossicles 325 via the coupling member 352. As such, movement/vibration of the ossicles 325 is captured by the implantable sound sensor 350 via the coupling member 352 (e.g., the mechanical coupling with the ossicles). The implantable sound sensor 350 is configured to covert the movement/vibration of the ossicles 325 into electrical signals representing the sound signal 333. These electrical signals, which are represented in FIG. 3 by arrow 357, are then provided to the implantable main module 334 via the lead 355.

As noted, the distal end 353 of the coupling member 352 is configured to be attached/secured to the recipient at, for example, the ossicles 325 of the recipient. In certain embodiments, the distal end 353 is bonded to the recipient using a bonding agent, such as a biocompatible cement or cement mixture, a rigid adhesive, etc. The resulting bond needs to relatively rigid bond so as to allow the vibrations to pass through to the coupling member 352.

The surgical process of bonding the distal end 353 of the coupling member 352 to the recipient can be challenging. For example, surgeons typically mix the bonding agent (e.g., cement) and then apply bonding agent to the distal end 353. If the bonding agent is mixed improperly (e.g., too fluidic or too inelastic), then the coupling member 352 can fail to properly bond to the ossicles 325, resulting in improper sound capture, subsequent detachment, etc. Moreover, if the bonding agent is too fluidic, then the bonding process could take longer, which introduces uncertainty as to how well the connection is forming. In addition, if the bonding agent spreads, the bonding agent may fix the middle ear to the inner wall of the middle ear cavity, which prevents proper sound capture by the implantable sound sensor 350 (e.g., ossicles 325 will not vibrate if bonded to the inner wall of the middle ear cavity). There is also risk that the surgeon can apply too much bonding agent, or apply bonding agent in an incorrect location, either of which can fix the coupling member 352 to, for example, the mastoid wall, etc., or cause other issues resulting in poor performance.

As such, presented herein are techniques to monitor a sensitivity of the implantable sound sensor 350 during the bonding process using signals captured/received by the implantable sound sensor 350. The monitoring is used to determine whether, when, and/or how the implantable sound sensor arrangement 349 is bonded to the ossicles 325.

FIG. 3 illustrates an example implementation of the techniques presented herein to monitor the bonding of the implantable sound sensor arrangement 349 to the ossicles 325. More specifically, in this example, the implantable sound sensor arrangement 349 and the implantable main module 334 form part of an internal/implantable component 312 of an implantable medical device system 302, where the implantable component 312 is implanted under the skin/tissue 315 of the recipient. In addition to the implantable sound sensor arrangement 349 and the implantable main module 334, the implantable component 312 could include, for example, a stimulation arrangement (not shown in FIG. 3). The stimulation arrangement could comprise, for example, one or more electrodes, a stimulating assembly, a mechanical stimulator, etc.

The implantable medical device system 302 of FIG. 3 also comprises an external component 304. In this example, the external component 304 comprises a sound processing unit 306 configured to be worn by the recipient and an in-the-ear (ITE) speaker (earphone speaker) 338 configured to be worn in the recipient's ear canal 335. The sound processing unit 306 is electrically connected to the earphone speaker 338 via a cable 339. Also shown in FIG. 3 is a computing device 310, which is also external to the recipient.

In accordance with embodiments presented herein, the surgeon initially attaches the distal end 353 of the coupling member 352 to the ossicles 325 with the bonding agent 358. While the bonding agent 358 cures (e.g., dries), sound signals, represented by arrow 344, are delivered to tympanic membrane 337 via the earphone speaker 338. In certain embodiments, the sound signals 344 can be initiated by the sound processing unit 306 based on commands/instructions received from the computing device 310. To this end, the sound processing unit 306 and the computing device 310 can be configured to communicate with one another via a communication link 326. The communication link 326 can be a wired link or wireless link, such as a Bluetooth link, Bluetooth Low Energy link, or other type of communication link.

The sound signals 344, when delivered to the tympanic membrane 337, cause vibration of the ossicles 325. While the bonding agent 358 is still curing, the implantable sound sensor 350 is activated (e.g., powered on and operational) and operates to capture the vibration of the ossicles 325 via the coupling member 352 (e.g., the mechanical coupling with the ossicles). The implantable sound sensor 350 coverts the sensed vibration of the ossicles 325 into electrical signals 357, which are then provided to the implantable main module 334 via the lead 355.

In this example, the implantable main module 334 and the sound processing unit 306 are configured to communicate with one another via a transcutaneous communication link 348. The communication link 348 can be, for example, a closely-coupled radio-frequency (RF) link, a magnetic induction (MI) link, a Bluetooth link, Bluetooth Low Energy, or other type of wireless communication link. The implantable main module 334 uses the communication link 348 to send "sound data" to the sound processing unit 348. The sound data, represented in FIG. 3 by arrow 349, can comprise, for example, the captured/received signals (as represented in the electrical signals 357) and/or other data associated with sound signals and/or data associated with the response of the implantable sound sensor 350 to the sound signals.

In the example of FIG. 3, the sound processing unit 306 uses the communication link 326 to send the sound data 346 to the computing device 310. The computing device 310 is configured to use the sound data 346 to generate an indication of the sensitivity of the implantable sound sensor 350 and, as such, an indication of the bond between the implantable sound sensor 350 and the ossicles 325, provided by the bonding agent 358, during and/or after the curing process. Example indications of the sensitivity of the implantable sound sensor 350 are described in greater detail below with reference to FIGS. 4A-6B.

As described above, the bond between implantable sound sensor 350 and ossicles 325 is monitored, as described above via the real-time sensitivity of the implantable sound sensor 350, while the bonding agent 358 is curing, and a final check can be performed after the bonding agent 358 has cured. In certain embodiments, the sensitivity of the implantable sound sensor 350 is measured. If the measured sensitivity values of the implantable sound sensor 350 are acceptable, then the surgical process can progress to a next stage and/or be completed (e.g., the surgical incision closed). As such, by the time the surgery has concluded, there is confidence that the implantable sound sensor 350 is operating at an acceptable level.

If the measured sensitivity of the implantable sound sensor 350 is not acceptable, then a clinical recommendation to perform a corrective action could be generated. The clinical recommendation (recommended corrective action) could be to check to see if the implantable sound sensor 350 is in the correct location, to dislocate the incudostapedial joint (e.g., dislocate the connection between the incus 345 and the stapes 347 of the ossicles 125), etc. Dislocating the incudostapedial joint, in particular, is used to make the ossicles (middle ear) 125 significantly more mobile, which helps particularly in older patients who already have contactive loss with a middle ear 125 that was previously not substantially mobile (ossification in the middle ear). Implanting the implantable sound sensor 350 also causes contactive loss because the middle ear 125 is not that mobile.

As noted above, FIG. 3 illustrates an example in which the earphone speaker 338 delivers the sound signals 344 to the recipient. It is to be appreciated that the use of an earphone speaker 338 to deliver the sound signals 344 is merely illustrative and that the sound signals could be delivered in other manners. For example, the sound signals 344 could be delivered by the computing device 310 (e.g., via internal speakers), via a speaker that is in the surgical theater, but not within the ear canal of the recipient, etc.

As noted above, FIGS. 4A-6B illustrate example indications of the bond between an implantable transducer, such as implantable sound sensor 350, and tissue (e.g., the ossicles 325) of a recipient. For ease of description, FIGS. 4A-6B will be described with reference to the bonding of the implantable sound sensor 350 to the ossicles 325 and associated components shown in FIG. 3.

Figure 4A:
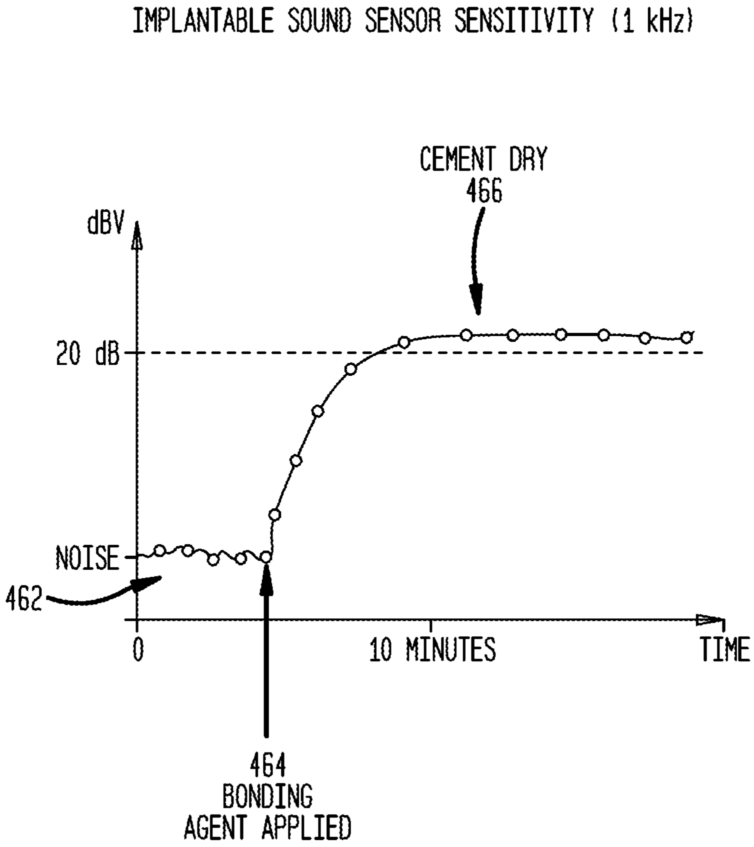
FIG. 4A is a graph illustrating an example indication of implantable sound sensor sensitivity, in accordance with certain embodiments presented herein.
Figure 4B:
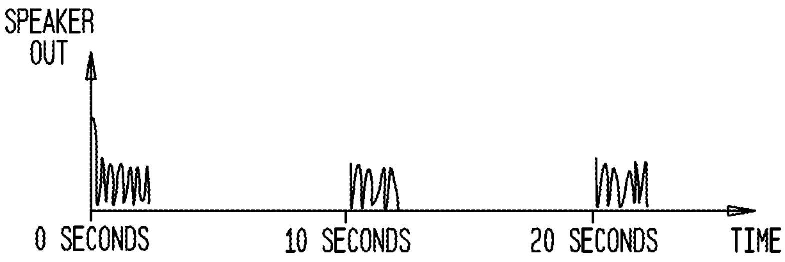
FIG. 4B is a graph illustrating sound signals delivered to a recipient for determining implantable sound sensor sensitivity, in accordance with certain embodiments presented herein.

Referring first to FIG. 4A, shown is a graph illustrating the output level (response) of the implantable sound sensor 350 over time. That is, the output level of the implantable sound sensor 350, in this example in voltage decibel (dBV), is shown on the vertical (y) axis of the graph shown in FIG. 4A, while time, in this example in minutes, is shown on the horizontal (z) axis. FIG. 4B is a graph corresponding to the example of FIG. 4A which illustrates delivery of sound signals 344 to the recipient. In particular, FIG. 4B illustrates an example in which the sound signals 344 comprise a 1 kHz test tone delivered to the recipient every 10 seconds.

Returning to FIG. 4A, the output of the implantable sensor 350 is measured periodically or continually at computing device 310 using the sound data 346 generated from the electrical signals 357 obtained from the implantable sound sensor 350. This measurement can begin when the implantable sensor 350 is implanted and before the bonding agent 358 is applied between the coupling member 352 and the ossicles 325. Measuring the output of the implantable sensor 350 prior to bonding the coupling member 352 to the ossicles 325 can provide a noise floor, represented in FIG. 4A at 462.

In FIG. 4A, at point 464, the bonding agent 358 is applied between the distal end 353 of the coupling member 352 and the ossicles 325. In the example of FIG. 4A, the measured output level of the implantable sensor 350 increases, over time, and then generally stabilizes at point 466. That is, the plotted curve 465 illustrates the change in the sensitivity of the implantable sensor 350 over time. Once the output level plateaus at 466, meaning the sensitivity of the implantable sound sensor 350 is relatively constant, the bonding agent 358 is cured.

In one example, the computing device 310 (e.g., software executed by the computing device 310) can display the graph of FIG. 4A, or a similar metric, to a user during the monitoring process. Such examples provide a visual representation of the bonding agent curing process. In the same or other examples, the computing device 310 is configured to automatically detect when the bonding agent 358 is cured and provide a corresponding indication, such as that shown in FIG. 4C, to the user. That is, FIG. 4C represents a specific example display that could be provided to a user via the display of the computing device 310, to indicate that "The Bonding Agent is Cured." It is to be appreciated that the computing device 310 could simultaneously or separately display the information shown in both FIG. 4A or 4C, or other information, to a user.

Figure 4C:
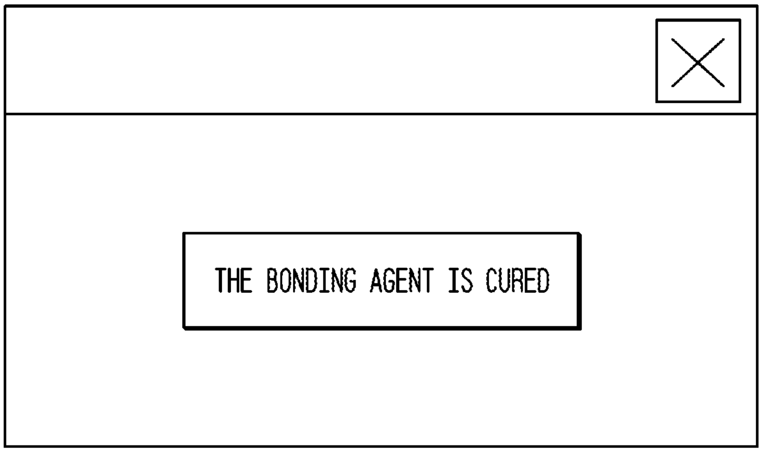
FIG. 4C is a schematic diagram illustrating a clinical recommendation based on a determined implantable sound sensor sensitivity, in accordance with certain embodiments presented herein.

In general, FIGS. 4A-4C illustrate that sensitivity of the implantable sound sensor 350 is measured/monitored while the bonding agent 358 cures. When the bonding agent 358 is cured (e.g., the sensitivity or output level of the implantable sound sensor 350 has stabilized), the stabilized output level of the implantable sound sensor 350 can be analyzed. In one example, the stabilized output level is compared to a threshold output level (e.g., low boundary). The computing device 310 can provide a clinical recommendation to a user based on the analysis of the stabilized output level of the implantable sound sensor 350. In certain examples, if the stabilized output level of the implantable sound sensor 350 is greater than the threshold output level, then the computing device 310 can indicate that the bonding is complete and/or that the surgeon can close the recipient. Alternatively, if the stabilized output level of the implantable sound sensor 350 is less than the threshold output level, the computing device 310 can provide a clinical recommendation to perform a corrective action, where the corrective action can depend upon the difference between the stabilized output level and the threshold output level. For example, the clinical recommendation to perform a corrective action can be to re-bond the coupling member 352 to the ossicles (or to correct the position or the angle) when, for example, the difference between the stabilized output level and the threshold output level is around 5-10 dBV (e.g., when the stabilized output level is 5-10 dB lower than the threshold output level). Alternatively, the clinical recommendation to perform a corrective action can be to dislocate the incudostapedial joint when, for example, the difference between the stabilized output level and the threshold output level is greater than 10 dBV (e.g., when the stabilized output level is more than 10 dB lower than the threshold output level).

Figure 5A:
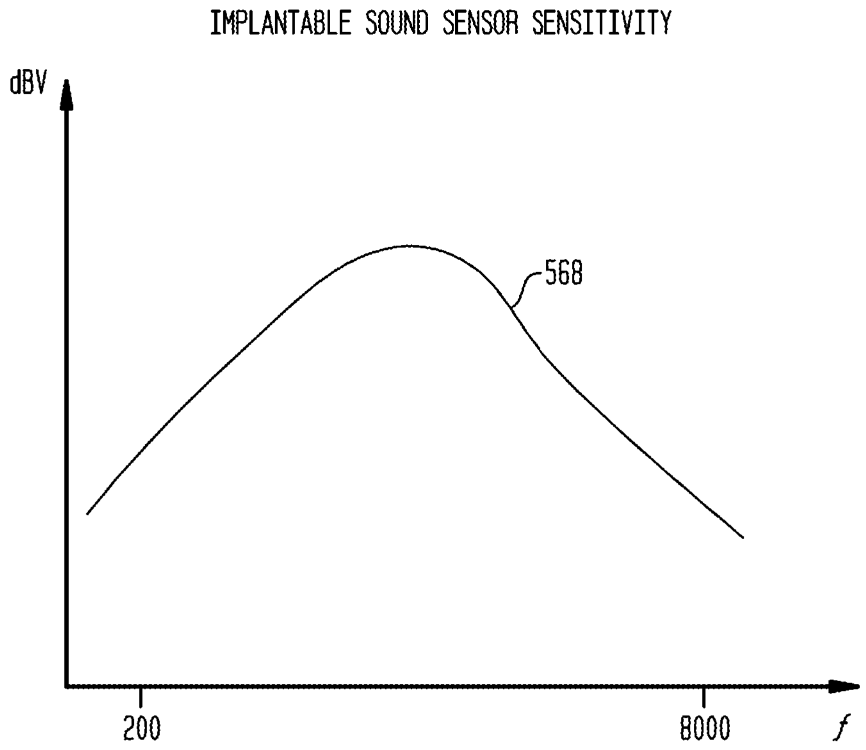
FIG. 5A is a graph illustrating an example indication of implantable sound sensor sensitivity, in accordance with certain embodiments presented herein.

FIG. 5A is a graph illustrating another indication of the sensitivity of the implantable sound sensor 350 across multiple frequencies. In this example, the computing device 310 uses the earphone speaker 338 to deliver sound signals 344 comprising a sweep in tone from about 200 Hz to 8 kHz test tone. At the same time, output of the implantable sensor 350 is measured, for each frequency, at computing device 310 using the sound data 346 generated from the electrical signals 357 obtained from the sound sensor. In other words, FIG. 5A illustrates that sound signals at a number of different frequencies, between a low frequency (200 Hz) and high frequency (8 kHz), are delivered to the recipient. The output of the implantable sound sensor 350 is recorded in response to each of the sound signals at the different frequencies. The measured output of the output of the implantable sensor 350, at each frequency, is plotted as curve 568 on the graph of FIG. 5A. In FIG. 5A, the output level of the implantable sound sensor 350, in this example in voltage decibel (dBV), is shown on the vertical (y) axis of the graph shown in FIG. 5A, while the frequency of the tone sweep is shown on the horizontal (z) axis.

In one example, the computing device 310 (e.g., software executed by the computing device 310) can display the graph of FIG. 5A, or a similar metric, to a user during the monitoring process. Such examples provide a visual representation of the frequency sensitivity of the implantable sound sensor 350. The computing device 310 could simultaneously or separately display the information shown in FIG. 5A, FIG. 4A, and/or 4C to a user.

FIG. 5A illustrates one example technique for measuring the frequency response of the implantable sound sensor 350. In an alternative embodiment, an MLS sequence can be used to measure and calculate the frequency response of the implantable sound sensor 350. In another embodiment, white noise or another type of sound signal can be used to measure and a FFT is performed to show the frequency response.

Figure 5B:
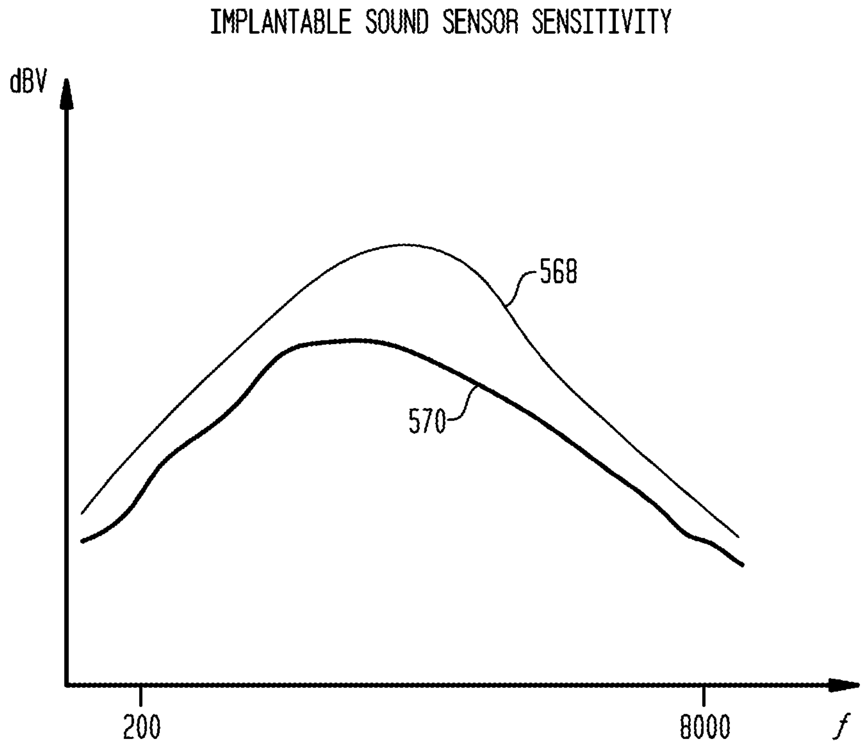
FIG. 5B is a graph illustrating an example indication of implantable sound sensor sensitivity, in accordance with certain embodiments presented herein.

FIG. 5A generally illustrates the frequency response of the implantable sound sensor 350 (e.g., sensitively across multiple frequencies), but does not provide an indication of whether the frequency response is acceptable. FIG. 5B is a graph illustrating the curve 568, representing the measured frequency response of the implantable sound sensor 350, with a threshold curve 570. In this example, the threshold curve 570 represents a minimum acceptable frequency response of an implantable sound sensor 350. As such, since measured curve 568 is above threshold curve 570 across the target frequency range (e.g., the measured frequency response is greater than the threshold frequency response), the measured curve 568 represents an acceptable frequency response of an implantable sound sensor 350.

Figure 5C:
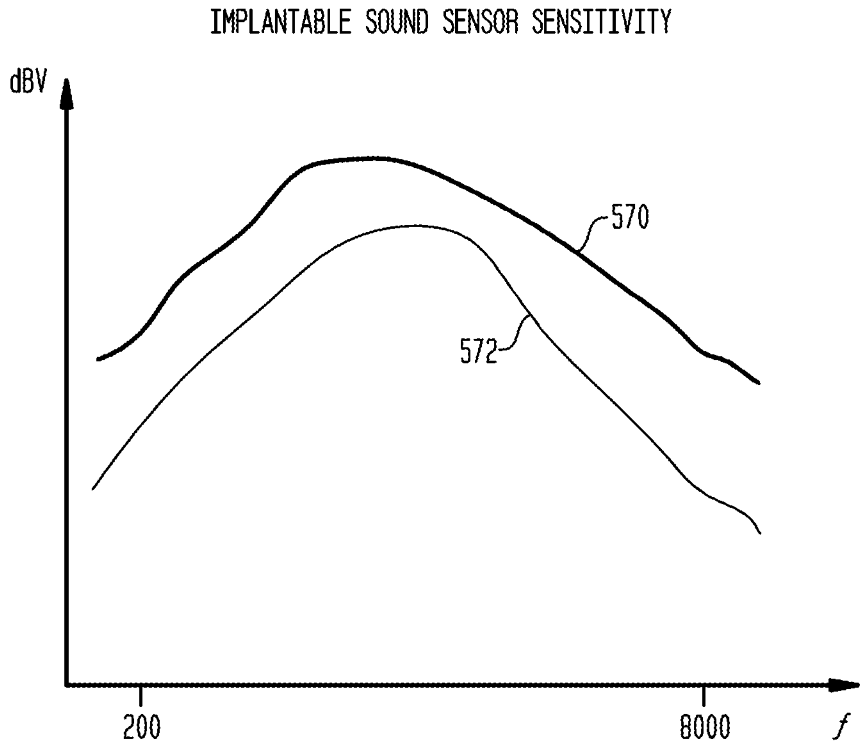
FIG. 5C is a graph illustrating an example indication of implantable sound sensor sensitivity, in accordance with certain embodiments presented herein.

FIG. 5C is a graph illustrating another curve 572, representing a different measured frequency response of the implantable sound sensor 350, with the threshold curve 570. Similar to FIG. 5B, the threshold curve 570 represents a minimum acceptable frequency response of the implantable sound sensor 350. As such, since curve 572 is below curve 570 across the target frequency range, the curve 572 represents an unacceptable frequency response of an implantable sound sensor 350 (e.g., the measured frequency response is less than the threshold frequency response). As such, the computing device 310 could determine that the frequency response of the implantable sound sensor 350, as represented by curve 572, is unacceptable. This could, in turn, cause the computing device 310 to recommend one or more remedial actions (e.g., generate one or more clinical recommendations).

Figure 6A:
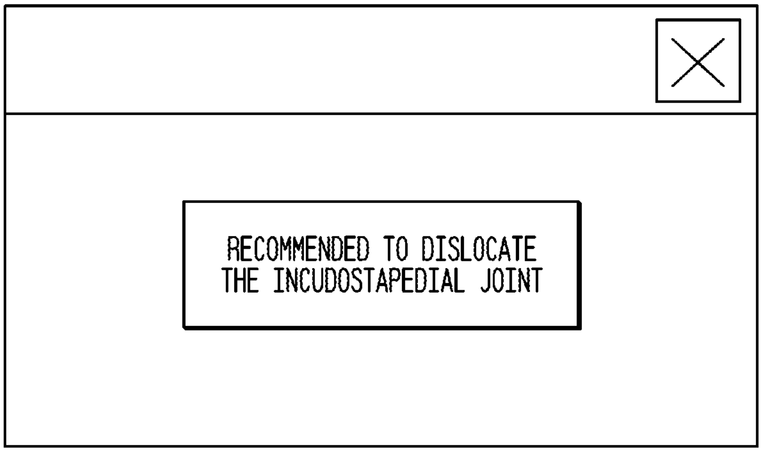
FIGS. 6A and 6B are schematic diagrams illustrating clinical recommendation based on a determined implantable sound sensor sensitivity, in accordance with certain embodiments presented herein.
Figure 6B:
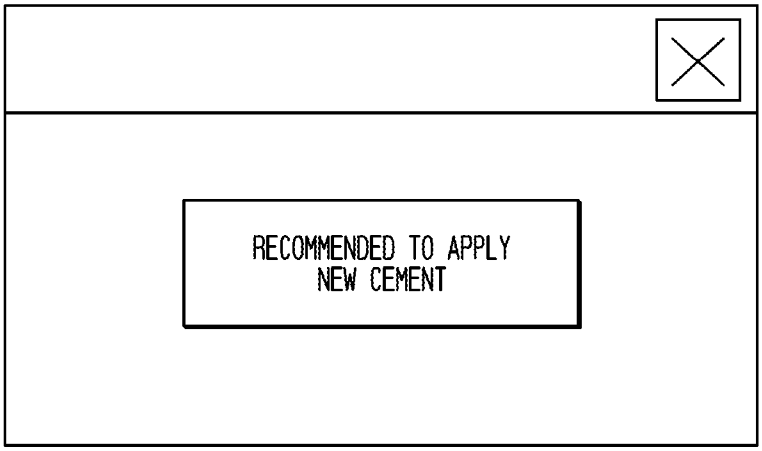

For example, FIGS. 6A and 6B illustrate example clinical recommendations 674(A) and 674(B), respectively, that could be displayed to a user via, for example, a display screen of the computing device 310. More specifically, the clinical recommendation 674(A) is a recommendation to dislocate the incudostapedial joint of the recipient. The clinical recommendation 674(B) is a recommendation to remove the bonding agent and re-bond the coupling member 352 to the ossicles 325.

In certain examples, the computing device 310 (e.g., software executed by the computing device 310) can display the graphs of FIG. 5A, 5B, or 5C, or a similar metric, to a user during the monitoring process. Such examples provide a visual representation of the bonding agent curing process and, specifically, the implantable sound sensor frequency response. In the same or other examples, the computing device 310 is configured to automatically determine the implantable sound sensor frequency response and provide a corresponding indication, such as that shown in FIG. 6A or 6B, to the user. The computing device 310 could simultaneously or separately display the information shown in both FIGS. 5A, 5B, 5C, 6A, and/or 6B to a user.

Moreover, in FIG. 4A, the sensitively of the implantable sound sensor 350 is shown at one frequency over time. In contrast, in FIGS. 5A, 5B, and 5C, the sensitively of the implantable sound sensor 350 is shown across multiple frequencies. As such, the examples of FIGS. 4A, 4C and 5A-5C show complementary sensitivity information that could be combined together (e.g., uses or shown simultaneously, separately, etc.) in different embodiments.

In one example presented herein, the implantable sound sensor 350 is implanted in the recipient. Prior to implantation, a user (e.g., surgeon) confirms that the implantable sound is functional. The surgeon determines that the implantable sound sensor 350 is not in contact with the ossicles 325 and attaches the coupling member 352 to the ossicles 325 with the bonding agent 358. The surgeon then visualizes/monitors the bonding agent 358 curing process, e.g., as described above with reference to FIGS. 4A-4C, to determine when the bonding agent is cured and/or to evaluate the stabilized response of the implantable sound sensor. When the bonding agent 358 is determined to be cured, the frequency response of the implantable sound sensor 350 can be measured, e.g., as described above with reference to FIGS. 5A-6B. The computing device 310 can provide the surgeon with a clinical recommendation based on the monitoring and/or measurement of the frequency.

As noted above, clinical recommendations in accordance with embodiments presented herein can take a number of different forms. In certain examples, if the monitoring indicates that the bonding agent has properly cured, the implantable sound sensor 350 has a sufficient stabilized response (e.g., the output level exceeds the threshold output level), and the implantable sound sensor 350 has an acceptable frequency response (e.g., the measured frequency response is greater than threshold frequency), the computing device 310 can provide a clinical recommendation to complete the surgery (e.g., indicate that the bonding is complete and/or that the surgeon can close the recipient).

Alternatively, if the monitoring indicates that the bonding agent has not properly cured, the implantable sound sensor 350 does not have sufficient stabilized response (e.g., the output level exceeds the threshold output level), and/or the implantable sound sensor 350 does not have an acceptable frequency response, then the computing device 310 can provide a clinical recommendation to perform a corrective action. For example, the clinical recommendation to perform a corrective action can be to re-bond the coupling member 352 to the ossicles, the clinical recommendation to perform a corrective action can be to dislocate the incudostapedial joint, etc. If a remedial action is taken, the monitoring process, as described above, can be repeated until the monitoring indicates that the bonding agent has properly cured, the implantable sound sensor 350 has a sufficient stabilized response (e.g., the output level exceeds the threshold output level), and the implantable sound sensor 350 has an acceptable frequency response. Thereafter, the surgeon can complete the surgery.

The examples of FIGS. 3, 4A-4C, 6A, and 6B have generally been described with reference to one specific arrangement of an implantable medical device system 200 comprising the implantable sound sensor 350. As noted elsewhere herein, aspects of the techniques presented herein can be implemented with a number of different implantable medical devices and implantable medical device systems comprising a number of different implantable transducers, including implantable sound sensors (e.g., implantable microphones), implantable vibration sensors, implantable actuators, etc.

Figure 7:
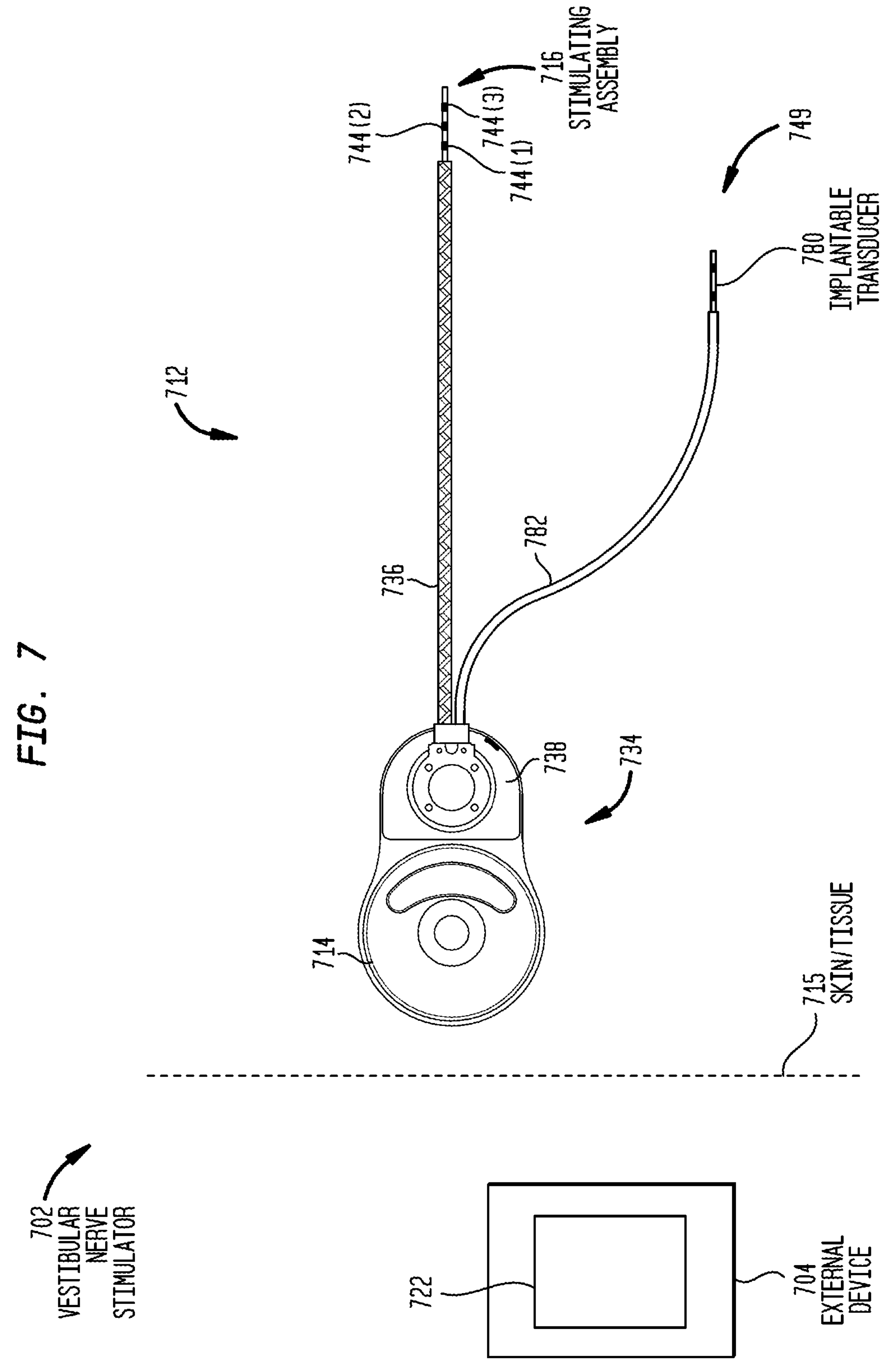
FIG. 7 is a schematic diagram illustrating a vestibular stimulator system with which aspects of the techniques presented herein can be implemented.

For example, FIG. 7 illustrates an example vestibular stimulator system 702, with which embodiments presented herein can be implemented. As shown, the vestibular stimulator system 702 comprises an implantable component (vestibular stimulator) 712 and an external device/component 704 (e.g., external processing device, battery charger, remote control, etc.). The external device 704 comprises an RF transmitter, receiver, and/or transceiver, referred to as a RF module 722. As such, the external device 704 is configured to transfer data (and potentially power) to the vestibular stimulator 712.

The vestibular stimulator 712 comprises an implant body (implantable main module 734) 734, a lead region 736, a stimulating assembly 716, and an implantable transducer arrangement 749, all configured to be implanted under the skin/tissue (tissue) 715 of the recipient. The implantable transducer arrangement 749 comprises an implantable transducer 780.

The implant body 734 generally comprises a hermetically-sealed housing 738 in which an RF module, one or more rechargeable batteries, one or more processors, and a stimulator unit are disposed. The implantable main module 734 also includes an internal/implantable coil 714 that is generally external to the housing 738, but which is connected to the RF module via a hermetic feedthrough (not shown).

The stimulating assembly 716 comprises a plurality of electrodes 744(1)-(3) disposed in a carrier member (e.g., a flexible silicone body). In this specific example, the stimulating assembly 716 comprises three (3) stimulation electrodes, referred to as stimulation electrodes 744(1), 744(2), and 744(3). The stimulation electrodes 744(1), 744(2), and 744(3) function as an electrical interface for delivery of electrical stimulation signals to the recipient's vestibular system.

The stimulating assembly 716 is configured such that a surgeon can implant the stimulating assembly adjacent the recipient's otolith organs via, for example, the recipient's oval window. It is to be appreciated that this specific embodiment with three stimulation electrodes is merely illustrative and that the techniques presented herein may be used with stimulating assemblies having different numbers of stimulation electrodes, stimulating assemblies having different lengths, etc.

As noted, the vestibular stimulator 712 also comprises an implantable transducer 780 that is electrically connected to the implantable main module 734 via a cable 782. The implantable transducer 780 can comprise, for example, an implantable sensor (e.g., vibration sensor, sound sensor, etc.) configured to capture signals from the body of the recipient or an actuator configured to deliver mechanical vibration to the body of the recipient.

In operation, the implantable transducer 780 is configured to be directly bonding to tissue of a recipient via bonding agent (not shown in FIG. 7) or bonded to a recipient via one or more intermediate devices, such as a coupling member, again using a bonding agent. In accordance with embodiments presented herein, during and after the curing of the bonding agent, signals can be delivered to the recipient and captured via the implantable transducer. In a similar way as described above with reference to FIGS. 3-6B, those signals captured by the implantable transducer 780 can be used to monitor the curing of the bonding agent. That is, the sensitivity of the implantable transducer 780 can be monitored to determine whether, when, and/or how well the implantable transducer 780 is bonded to the tissue of the recipient.

Figure 8:
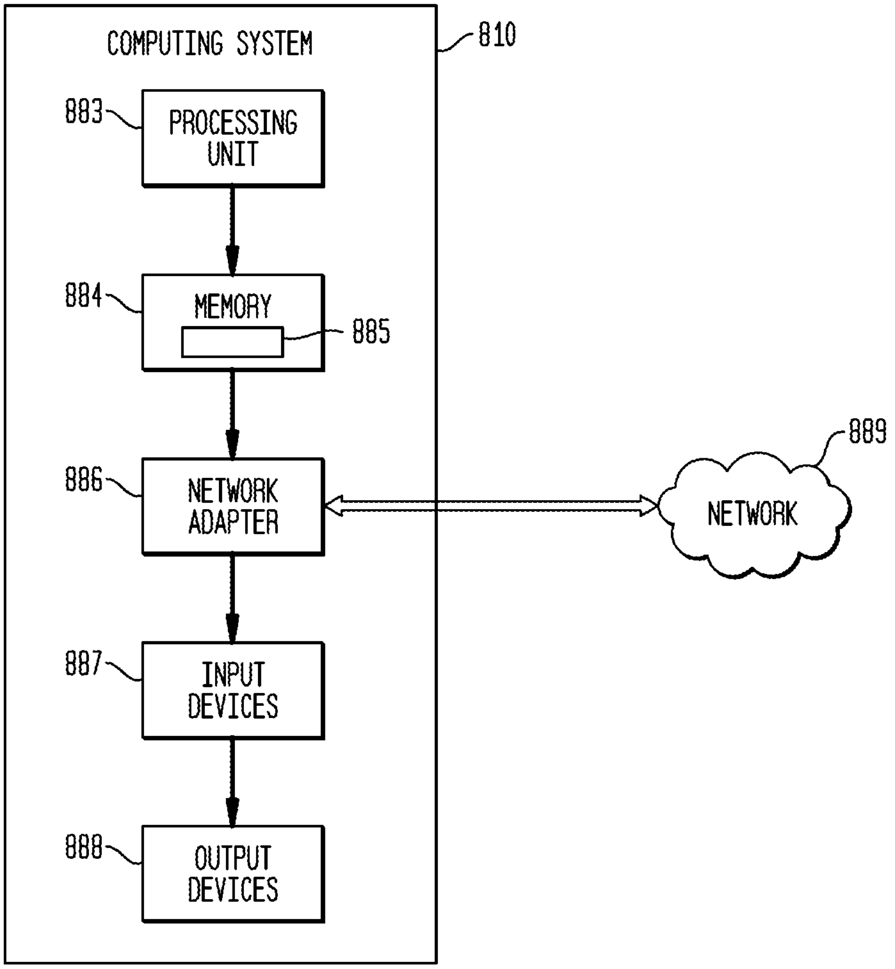
FIG. 8 is a schematic diagram illustrating a computing system with which aspects of the techniques presented herein can be implemented.

As noted above, aspects of the techniques presented make use of a computing device (e.g., computing device 310 in FIG. 3). FIG. 8 illustrates an example of a suitable computing system 810 with which one or more of the disclosed examples can be implemented. Computing systems, environments, or configurations that can be suitable for use with examples described herein include, but are not limited to, personal computers, server computers, hand-held devices, laptop devices, multiprocessor systems, microprocessor-based systems, programmable consumer electronics (e.g., smart phones), network PCs, minicomputers, mainframe computers, tablets, distributed computing environments that include any of the above systems or devices, and the like. The computing system 810 can be a single virtual or physical device operating in a networked environment over communication links to one or more remote devices, such as an implantable medical device or implantable medical device system.

In its most basic configuration, computing system 810 includes at least one processing unit 883 and memory 884. The processing unit 883 includes one or more hardware or software processors (e.g., Central Processing Units) that can obtain and execute instructions. The processing unit 883 can communicate with and control the performance of other components of the computing system 810.

The memory 884 is one or more software or hardware-based computer-readable storage media operable to store information accessible by the processing unit 883. The memory 884 can store, among other things, instructions executable by the processing unit 883 to implement applications or cause performance of operations described herein, as well as other data. The memory 884 can be volatile memory (e.g., RAM), non-volatile memory (e.g., ROM), or combinations thereof. The memory 884 can include transitory memory or non-transitory memory. The memory 884 can also include one or more removable or non-removable storage devices. In examples, the memory 884 can include RAM, ROM, EEPROM (Electronically-Erasable Programmable Read-Only Memory), flash memory, optical disc storage, magnetic storage, solid state storage, or any other memory media usable to store information for later access. In examples, the memory 884 encompasses a modulated data signal (e.g., a signal that has one or more of its characteristics set or changed in such a manner as to encode information in the signal), such as a carrier wave or other transport mechanism and includes any information delivery media. By way of example, and not limitation, the memory 884 can include wired media such as a wired network or direct-wired connection, and wireless media such as acoustic, RF, infrared and other wireless media or combinations thereof. In certain embodiments, the memory 884 comprises implantable transducer monitoring logic 885 that, when executed, enables the processing unit 883 to perform aspects of the techniques presented.

In the illustrated example, the system 810 further includes a network adapter 886, one or more input devices 887, and one or more output devices 888. The system 810 can include other components, such as a system bus, component interfaces, a graphics system, a power source (e.g., a battery), among other components.

The network adapter 886 is a component of the computing system 810 that provides network access (e.g., access to at least one network 889). The network adapter 886 can provide wired or wireless network access and can support one or more of a variety of communication technologies and protocols, such as ETHERNET, cellular, BLUETOOTH, near-field communication, and RF (Radiofrequency), among others. The network adapter 886 can include one or more antennas and associated components configured for wireless communication according to one or more wireless communication technologies and protocols.

The one or more input devices 887 are devices over which the computing system 810 receives input from a user. The one or more input devices 887 can include physically-actuatable user-interface elements (e.g., buttons, switches, or dials), touch screens, keyboards, mice, pens, and voice input devices, among others input devices.

The one or more output devices 888 are devices by which the computing system 810 is able to provide output to a user. The output devices 888 can include, displays, speakers, and printers, among other output devices.

It is to be appreciated that the arrangement for computing system 810 shown in FIG. 8 is merely illustrative and that aspects of the techniques presented herein may be implemented at a number of different types of systems/devices. For example, the computing system 810 could be a laptop computer, tablet computer, mobile phone, surgical system, etc.

Figure 9:
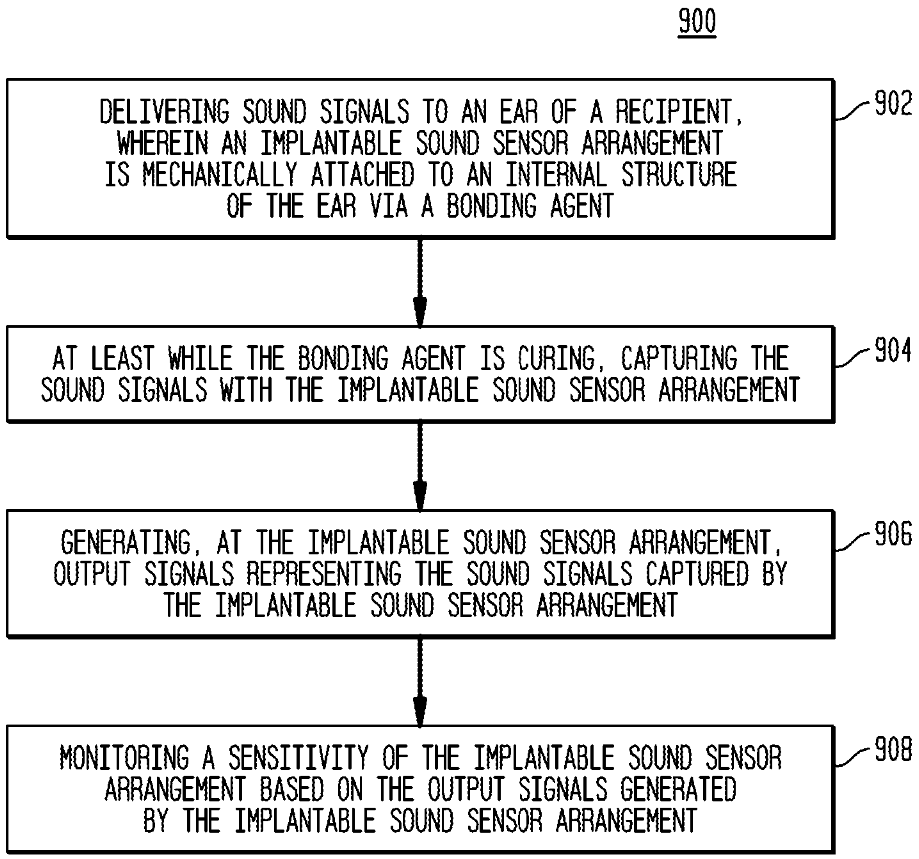
FIG. 9 is a flowchart illustrating an example method, in accordance with certain embodiments presented herein.

FIG. 9 is a flowchart of an example method 900, in accordance with embodiments presented herein. Method 900 begins at 902 where sound signals are delivered to an ear of a recipient, wherein an implantable sound sensor arrangement is mechanically attached to an internal structure of the ear via a bonding agent. At 904, at least while the bonding agent is curing, the implantable sound sensor arrangement captures the sound signals. At 906, the implantable sound sensor arrangement generates output signals representing the sound signals captured by the implantable sound sensor arrangement. At 908, a sensitivity of the implantable sound sensor arrangement is monitored based on the output signals generated by the implantable sound sensor arrangement.

Figure 10:
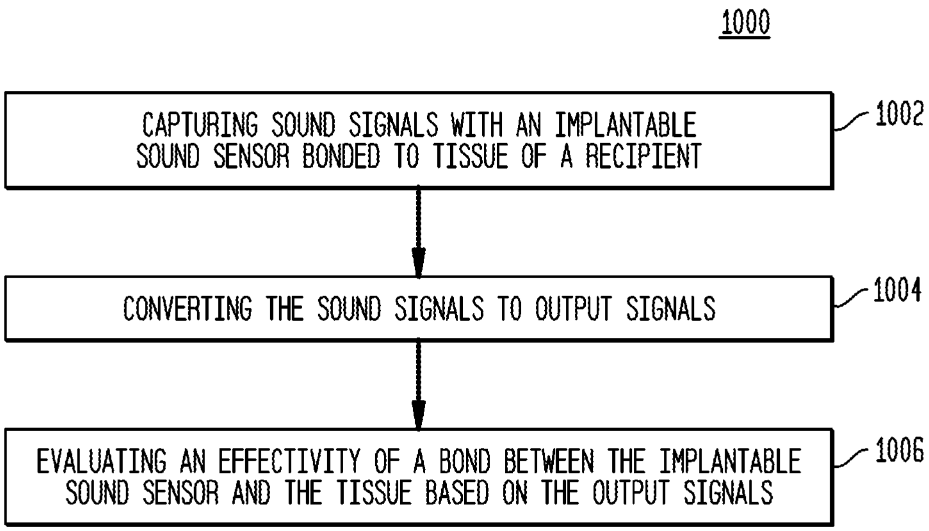
FIG. 10 is a flowchart illustrating another example method, in accordance with certain embodiments presented herein.

FIG. 10 is a flowchart of an example method 1000, in accordance with embodiments presented herein. Method 1000 begins at 1002 where sound signals are captured with an implantable sound sensor bonded to tissue of a recipient. At 1004, the sound signals are converted to output signals. At 1006, an effectivity of a bond between the implantable sound sensor and the tissue based is evaluated on the output signals.

As should be appreciated, while particular uses of the technology have been illustrated and discussed above, the disclosed technology can be used with a variety of devices in accordance with many examples of the technology. The above discussion is not meant to suggest that the disclosed technology is only suitable for implementation within systems akin to that illustrated in the figures. In general, additional configurations can be used to practice the processes and systems herein and/or some aspects described can be excluded without departing from the processes and systems disclosed herein.

This disclosure described some aspects of the present technology with reference to the accompanying drawings, in which only some of the possible aspects were shown. Other aspects can, however, be embodied in many different forms and should not be construed as limited to the aspects set forth herein. Rather, these aspects were provided so that this disclosure was thorough and complete and fully conveyed the scope of the possible aspects to those skilled in the art.

As should be appreciated, the various aspects (e.g., portions, components, etc.) described with respect to the figures herein are not intended to limit the systems and processes to the particular aspects described. Accordingly, additional configurations can be used to practice the methods and systems herein and/or some aspects described can be excluded without departing from the methods and systems disclosed herein.

According to certain aspects, systems and non-transitory computer readable storage media are provided. The systems are configured with hardware configured to execute operations analogous to the methods of the present disclosure. The one or more non-transitory computer readable storage media comprise instructions that, when executed by one or more processors, cause the one or more processors to execute operations analogous to the methods of the present disclosure.

Similarly, where steps of a process are disclosed, those steps are described for purposes of illustrating the present methods and systems and are not intended to limit the disclosure to a particular sequence of steps. For example, the steps can be performed in differing order, two or more steps can be performed concurrently, additional steps can be performed, and disclosed steps can be excluded without departing from the present disclosure. Further, the disclosed processes can be repeated.

Although specific aspects were described herein, the scope of the technology is not limited to those specific aspects. One skilled in the art will recognize other aspects or improvements that are within the scope of the present technology. Therefore, the specific structure, acts, or media are disclosed only as illustrative aspects. The scope of the technology is defined by the following claims and any equivalents therein.

It is also to be appreciated that the embodiments presented herein are not mutually exclusive and that the various embodiments may be combined with another in any of a number of different manners.

What is claimed is:

1. A method comprising:

delivering sound signals to an ear of a recipient, wherein an implantable sound sensor arrangement is mechanically attached to an internal structure of the ear via a bonding agent;

at least while the bonding agent is curing, capturing the sound signals with the implantable sound sensor arrangement;

generating, at the implantable sound sensor arrangement, output signals representing the sound signals captured by the implantable sound sensor arrangement; and monitoring a sensitivity of the implantable sound sensor arrangement based on the output signals generated by the implantable sound sensor arrangement.

2. The method of claim 1, further comprising:

at least while the bonding agent is curing, displaying, at a computing device, a visual representation of the sensitivity of the implantable sound sensor arrangement.

3. The method of claim 2, wherein displaying the visual representation of the sensitivity of the implantable sound sensor arrangement comprises:

displaying a measured level of the output signals generated by the implantable sound sensor arrangement, over time, in response to the sound signals.

4. The method of claim 1, wherein delivering the sound signals to the ear of the recipient comprises:

periodically delivering sound signals having a substantially constant frequency and a substantially constant amplitude.

5. The method of claim 2, wherein displaying the visual representation of the sensitivity of the implantable sound sensor arrangement comprises:

determining a frequency response of the implantable sound sensor arrangement based on the output signals generated by the implantable sound sensor arrangement; and displaying the frequency response of the implantable sound sensor arrangement.

6. The method of claim 5, wherein delivering the sound signals to the ear of the recipient comprises:

delivering sound signals having a substantially constant amplitude at a plurality of different frequencies between a first frequency and a second frequency.

7. The method according to claim 1, wherein monitoring the sensitivity of the implantable sound sensor arrangement based on the output signals generated by the implantable sound sensor arrangement comprises:

determining whether a level of the output signals generated by the implantable sound sensor arrangement exceeds a predetermined threshold level.

8. The method according to claim 7, further comprising:

when the level of the output signals generated by the implantable sound sensor arrangement exceeds the predetermined threshold level, outputting an indication of a successful bond between the implantable sound sensor arrangement and the internal structure of the ear, or when the level of the output signals generated by the implantable sound sensor arrangement does not exceed the predetermined threshold level, outputting a clinical recommendation to perform a corrective action.

9. The method according to claim 7, wherein outputting a clinical recommendation to perform a corrective action comprises at least one of:

outputting a clinical recommendation to re-bond the implantable sound sensor arrangement to the internal structure of the ear, or outputting a clinical recommendation to dislocate an incudostapedial joint of the ear.

10. The method according to claim 1, wherein monitoring the sensitivity of the implantable sound sensor arrangement based on the output signals generated by the implantable sound sensor arrangement comprises:

determining whether a frequency response of the implantable sound sensor arrangement exceeds a predetermined frequency response.

11. The method of claim 1, further comprising:

generating a clinical recommendation based on the sensitivity of the implantable sound sensor arrangement.

12. One or more non-transitory computer readable storage media comprising instructions that, when executed by a processor, cause the processor to:

receive output signals captured by an implantable sound sensor arrangement that is mechanically attached to an internal structure of an ear of a recipient via a bonding agent, wherein the output signals represent sound signals captured by the implantable sound sensor arrangement at least while the bonding agent is curing; and monitoring a sensitivity of the implantable sound sensor arrangement based on the output signals generated by the implantable sound sensor arrangement.

13. The non-transitory computer readable storage media of claim 12, wherein the instructions operable to monitor the sensitivity of the implantable sound sensor arrangement based on the output signals comprise instructions operable to:

determine whether a level of the sound signals captured by the implantable sound sensor arrangement exceeds a predetermined threshold.

14. The non-transitory computer readable storage media of claim 12, wherein the instructions operable to determine the sensitivity of the implantable sound sensor arrangement based on the output signals comprise instructions operable to:

determine whether a level of the sound signals stabilizes.

15. The non-transitory computer readable storage media of claim 12, further comprising instructions operable to:

deliver the sound signals to an ear of the recipient via a speaker; and record an output of the implantable sound sensor arrangement, wherein the sensitivity of the implantable sound sensor arrangement is determined from the output of the implantable sound sensor arrangement.

16. The non-transitory computer readable storage media of claim 12, further comprising instructions operable to:

output, to a display, an indication of the sensitivity of the implantable sound sensor arrangement.

17. The non-transitory computer readable storage media according to claim 16, wherein the instructions operable to output an indication of the sensitivity of the implantable sound sensor arrangement comprise instructions operable to:

output an indication of an effectivity of a bond between the implantable sound sensor arrangement and the internal structure of the ear.

18. The non-transitory computer readable storage media according to claim 16, wherein the instructions operable to output the indication of the sensitivity of the implantable sound sensor arrangement comprise instructions operable to:

determine whether a decibel level of the sound signals exceeds a predetermined threshold; and when the decibel level of the sound signals exceeds the predetermined threshold, output an indication of a successful bond between the implantable sound sensor arrangement and the internal structure of the ear.

19. The non-transitory computer readable storage media according to claim 16, wherein the instructions operable to output the indication of the sensitivity of the implantable sound sensor arrangement comprise instructions operable to:

determine whether a decibel level of the sound signals exceeds a predetermined threshold; and when the decibel level of the sound signals does not exceed the predetermined threshold, output an indication of a failed bond between the implantable sound sensor arrangement and the internal structure of the ear.

20. The non-transitory computer readable storage media according to claim 12, wherein instructions operable to receive the sound signals captured by the implantable sound sensor arrangement bonded to human tissue comprise instructions operable to:

receive sound signals having a predetermined frequency tone.

21. The non-transitory computer readable storage media according to claim 12, wherein the instructions operable to receive output signals captured by the implantable sound sensor arrangement comprise instructions operable to:

receive output signals associated with sound signals at least a first frequency and a second frequency.

22. The non-transitory computer readable storage media according to claim 12, wherein the instructions operable to receive output signals captured by the implantable sound sensor arrangement comprise instructions operable to:

receive output signals associated with sound signals having a sequence of frequency tones.

* * * * *